US00PP09289P

United States Patent [19]

Wathen

[11] Patent Number: Plant 9,289

[45] Date of Patent: Sep. 19, 1995

[54] HYBRID TEA ROSE PLANT NAMED 'WEKSLATS'

[75] Inventor: Evan H. Wathen, Beaumont, Tex.

[73] Assignee: Weeks Wholesale Rose Growers, Inc., Upland, Calif.

[21] Appl. No.: 303,483

[22] Filed: Sep. 9, 1994

[51] Int. Cl.[6] ..... A01H 5/00
[52] U.S. Cl. ..... Plt./18
[58] Field of Search ..... Plt. 11, 18, 14

[56] References Cited

U.S. PATENT DOCUMENTS

| | | | |
|---|---|---|---|
| P.P. 79 | 11/1933 | Weigand | Plt./18 |
| P.P. 121 | 2/1935 | Kaucher | Plt./18 |
| P.P. 6,714 | 4/1989 | Christensen et al. | Plt./14 |

*Primary Examiner*—Howard J. Locker
*Attorney, Agent, or Firm*—Christie, Parker & Hale

[57] ABSTRACT

A new variety of Hybrid Tea rose suitable for greenhouse culture and garden decoration, having flowers of light lavender pink coloration.

1 Drawing Sheet

BACKGROUND OF THE INVENTION

This invention relates to a new and distinct variety of Hybrid Tea rose. The varietal denomination of the new variety is 'Wekslats'. The plant is a bushy upright plant, cultivated for outdoor garden decoration and greenhouse cultivation. It was discovered as a naturally occurring mutation of the parent cultivar 'Arobipy' (U.S. Plant Pat. No. 6,714), the disclosure of which is hereby expressly incorporated by reference.

SUMMARY OF THE INVENTION

Among the features which distinguish the new variety 'Wekslats' from other presently available and known commercial rose cultivars is the abundant production of long-stemmed large fragrant flowers of light lavender pink coloration; 'Wekslats' may be asexually propagated by cuttings, budding, grafting, layering and tissue culture.

Asexual reproduction of the new variety as performed by vegetative cutting, budding and grafting in Kern County and Upland, Calif., shows that the foregoing and other distinguishing characteristics come true to form and are established and transmitted through succeeding propagations.

COMPARISON WITH PARENT VARIETIES

The new rose may be distinguished from its parent, 'Arobipy', by the following combination of characteristics: whereas 'Arobipy' produces flowers of predominantly white coloration, 'Wekslats' produces flowers of a distinct soft lavender pink coloration. 'Wekslats' flowers emit a strong sweet fragrance, whereas the parent's flowers have only a moderate spicy fragrance.

BRIEF DESCRIPTION OF THE ILLUSTRATION

The accompanying photograph illustrates flowers and foliage of the plant in color and shows the flowering thereof from bud to full bloom in color as nearly correct as it is possible to make in a color illustration of the character. In the illustration, flowers of the new variety are contrasted with flowers of 'Arobipy' which are the two lowermost flowers in the illustration. As can be seen, the 'Arobipy' flowers are near white and flowers of 'Wekslats' are light lavender pink. Throughout this specification, color values are based upon the Colour Chart of The Royal Horticultural Society of London, England (RHS) except where common terms of color definition are employed.

DESCRIPTION OF THE NEW VARIETY

The following description is of rose plants of the new cultivar grown in a greenhouse in Upland, Calif. in the month of May. Phenotypic expression may vary with environmental, cultural and climatic conditions, as well as differences in conditions of light and soil.

FLOWER

The flowers have a strong sweet fragrance.

BUD

The color of the undersurfaces of the newly opened petals is between 69A and 65C. The color of the upper surfaces of the newly opened petals is between 69B and 65D.

NEWLY OPENED FLOWER

The undersurface of the outer, intermediate and inner petals is between 69C and 65D. The upper surface of the outer, intermediate and inner petals is between 69D and 69C.

The general tonality of the newly opened flower is near to between 69C and 69D.

THREE-DAY-OLD FLOWER

The under and upper surface of the outer and intermediate petals is lighter than between 69D and 76D.

The general tonality of the three-day-old flower is lighter than between 69D and 76D.

In all other significant respects, the new variety resembles its parent.

I claim:

1. A new and distinct variety of Hybrid Tea rose plant substantially as described and illustrated herein.

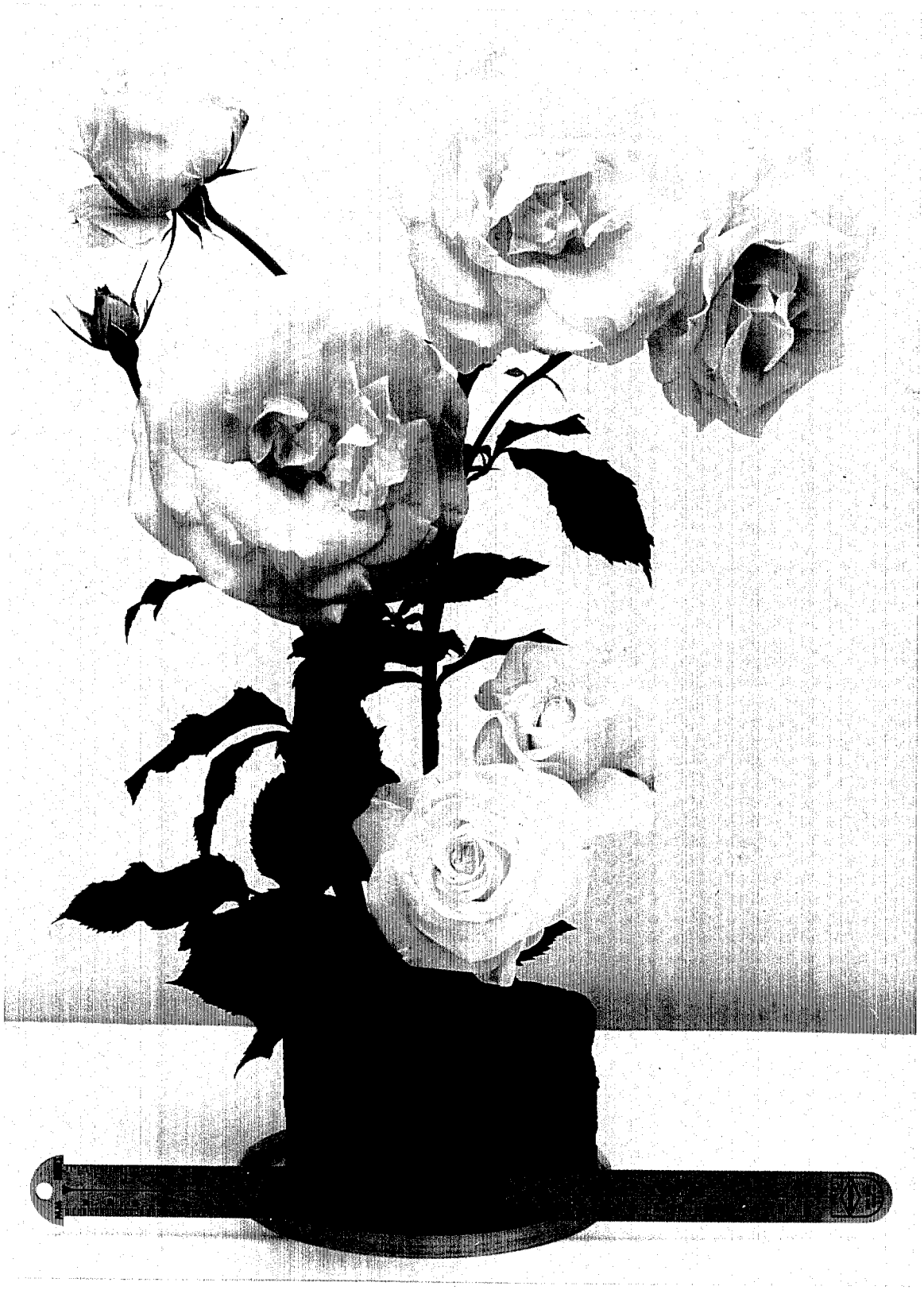

* * * * *